United States Patent
Hashmi et al.

(10) Patent No.: US 10,737,994 B2
(45) Date of Patent: Aug. 11, 2020

(54) ACETONE PURIFICATION SYSTEMS AND METHODS

(71) Applicant: SABIC Global Technologies B.V., Bergen op Zoom (NL)

(72) Inventors: Syed Azhar Hashmi, Riyadh (SA); Salkod Parameshwar Mallika, Bangalore (IN); Flaiyh Al-Anazi, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 31 days.

(21) Appl. No.: 16/316,644

(22) PCT Filed: Jul. 12, 2017

(86) PCT No.: PCT/IB2017/054212
§ 371 (c)(1),
(2) Date: Jan. 10, 2019

(87) PCT Pub. No.: WO2018/011733
PCT Pub. Date: Jan. 18, 2018

(65) Prior Publication Data
US 2020/0181054 A1    Jun. 11, 2020

Related U.S. Application Data

(60) Provisional application No. 62/361,156, filed on Jul. 12, 2016.

(51) Int. Cl.
| | | |
|---|---|---|
| C07C 45/79 | (2006.01) |
| B01J 41/05 | (2017.01) |
| B01D 15/36 | (2006.01) |
| B01J 41/14 | (2006.01) |
| B01J 47/02 | (2017.01) |
| B01J 41/20 | (2006.01) |

(52) U.S. Cl.
CPC ............ *C07C 45/79* (2013.01); *B01D 15/363* (2013.01); *B01J 41/05* (2017.01); *B01J 41/14* (2013.01); *B01J 41/20* (2013.01); *B01J 47/02* (2013.01)

(58) Field of Classification Search
CPC .................................................... C07C 45/79
See application file for complete search history.

(56) References Cited

U.S. PATENT DOCUMENTS

| | | | |
|---|---|---|---|
| 2,624,699 A | 1/1953 | Joris | |
| 3,168,571 A | 2/1965 | Hare | |
| 4,340,447 A | 7/1982 | Laverick et al. | |
| 4,722,769 A | 2/1988 | Chan et al. | |
| 5,399,776 A * | 3/1995 | Fraini | C07C 45/85 568/411 |
| 5,788,818 A | 8/1998 | Lorenzoni et al. | |
| 7,390,919 B1 | 6/2008 | Salisbury et al. | |
| 7,416,645 B2 | 8/2008 | Weber et al. | |
| 2008/0214872 A1 | 9/2008 | Nelson et al. | |
| 2008/0214873 A1 | 9/2008 | Nelson et al. | |
| 2010/0140075 A1 | 6/2010 | Nelson et al. | |
| 2010/0145103 A1 | 6/2010 | Nelson et al. | |
| 2014/0121404 A1 | 5/2014 | Hallinan et al. | |

FOREIGN PATENT DOCUMENTS

| | | |
|---|---|---|
| CA | 1016100 A1 | 8/1977 |
| CN | 101973859 A | 2/2011 |
| EP | 767160 A1 | 4/1997 |
| EP | 1188737 A1 | 3/2002 |
| KR | 100881279 B1 | 2/2009 |
| WO | 0153242 A1 | 7/2001 |

OTHER PUBLICATIONS

Chinese Patent No. 101973859; Date of Publication: Feb. 16, 2011; Abstract Only, 2 pages.
Dowex, Ion Exchange Resins—Powerful Chemical Processing Tools; Dow Liquid Separations; 2002; 12pages.
European Patent No. 1188737; Date of Publication: Mar. 20, 2002; Abstract Only, 2 pages.
International Search Report for International Application No. PCT/IB2017/054212; dated Oct. 5, 2017; 5 pages.
Korean Patent No. 100881279; Date of Publication: Feb. 3, 2009; Abstract Only, 1 page.
Written Opinion of the International Search Report for International Application No. PCT/IB2017/054212; dated Oct. 5, 2017; 6 pages.

\* cited by examiner

*Primary Examiner* — Sikarl A Witherspoon
(74) *Attorney, Agent, or Firm* — Cantor Colburn LLP

(57) ABSTRACT

A method for purifying acetone includes contacting an initial solution with a basic ion-exchange resin at a temperature of 15° C. to 30° C., wherein the initial solution comprises acetone and acetone impurities; and removing the acetone impurities from the initial solution with the basic ion-exchange resin to produce a purified solution.

15 Claims, 1 Drawing Sheet

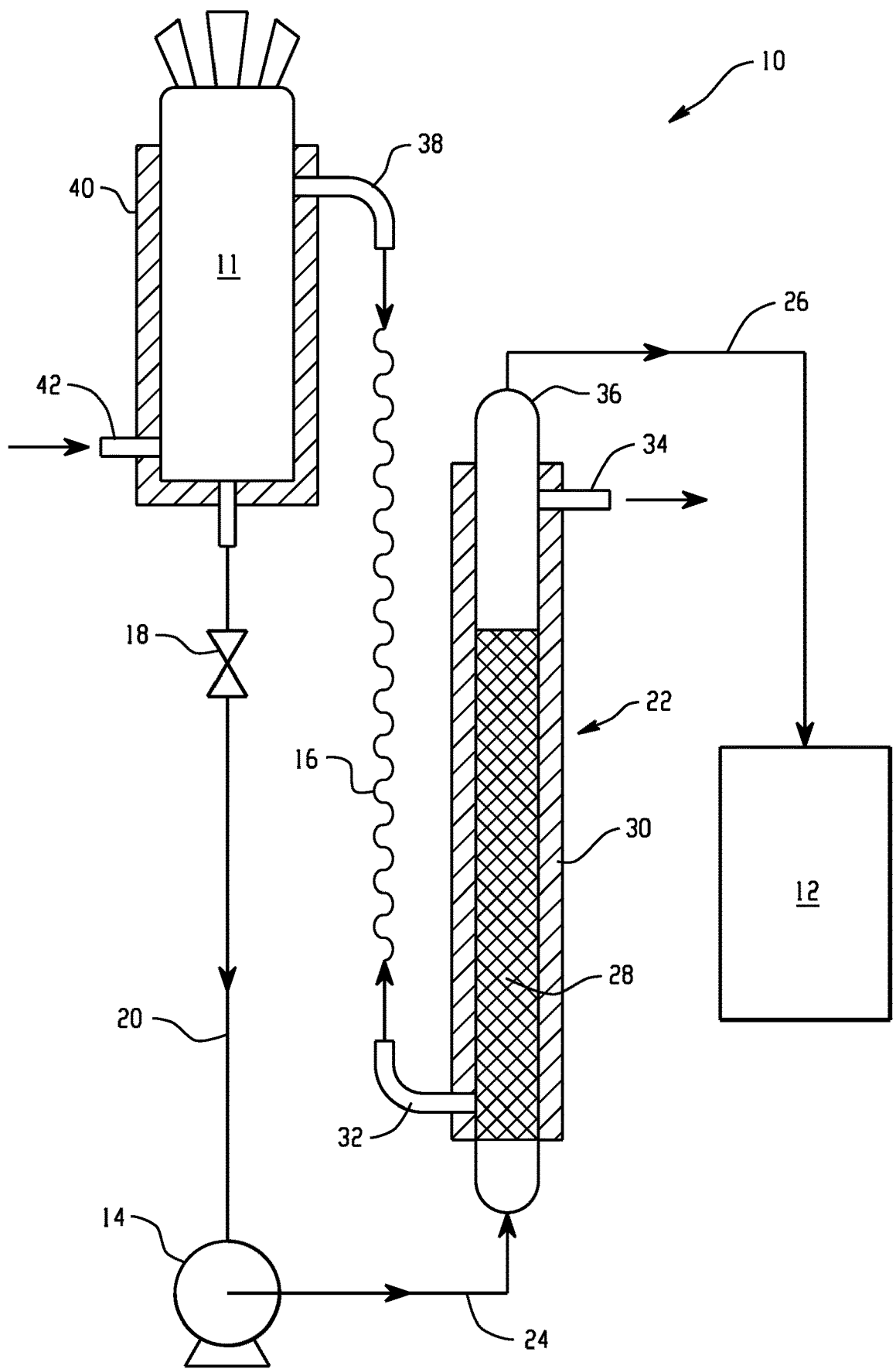

ACETONE PURIFICATION SYSTEMS AND METHODS

CROSS REFERENCE TO RELATED APPLICATIONS

This application is a 371 of International Application No. PCT/IB2017/054212, filed Jul. 12, 2017, which claims priority to U.S. Application No. 62/361,156 filed Jul. 12, 2016, both of which are incorporated herein by reference in their entirety.

BACKGROUND

Acetone is produced in a number of ways most of which result in an acetone solution having additional undesirable by-products or impurities. For example, acetone can be produced together with phenol during the decomposition of cumene hydroperoxide. In such example, the decomposition products are fed into a fractionation column, in which the products are separated into a crude acetone solution and a crude phenol solution.

Crude acetone generally contains aldehyde impurities that must be removed to produce a purified acetone solution. Various methods exist for purifying acetone, but each has their disadvantages. For example, crude acetone can be treated by using simple distillation. However, a distillation method alone is not completely effective because impurities, specifically, aliphatic aldehydes, olefins, and a whole series of other impurities, remain in the treated acetone product, reducing its purity and quality.

Another known method of purifying acetone involves distilling crude acetone in two separate columns. In such method, the low molecular weight impurities are isolated in the first rectification column with the addition of an alkaline reagent to the first column. The remaining mixture is fed to the second rectification column to separate high molecular weight impurities, producing commercial acetone. However, such method requires the second rectification column to operate at pressures below atmospheric pressure, which significantly increases operating costs and reduces the productivity of the second column compared to a column operated at atmospheric pressure.

There is a need to provide a simple and cost effective method for removing impurities from crude acetone without sacrificing the purity of the treated acetone.

BRIEF DESCRIPTION

Disclosed herein are systems and methods of purifying an acetone solution.

A method for purifying acetone comprises: contacting an initial solution with a basic ion-exchange resin at a temperature of 15° C. to 30° C., wherein the initial solution comprises acetone and acetone impurities; and removing the acetone impurities from the initial solution with the basic ion-exchange resin to produce a purified solution.

An acetone purification system comprises: a reactor comprising an initial solution comprising acetone and acetone impurities; a column comprising an ion-exchange resin, wherein the column is connected to the reactor by a first line, wherein the first line includes a pump that directs the initial solution through the column to contact the basic ion-exchange resin; and a container for collecting a purified solution from the column, wherein the container is connected to the column by a second line.

The above described and other features are exemplified by the following figures and detailed description.

BRIEF DESCRIPTION OF THE DRAWINGS

Refer now to the FIGURE, which are exemplary embodiments, and wherein the like elements are numbered alike.

FIG. 1 illustrates a schematic of an embodiment of the apparatus disclosed herein.

DETAILED DESCRIPTION

The present systems and methods relate to the purification of acetone solutions that contain aldehyde impurities, such as acetaldehyde and propionaldehyde. The systems and methods are particularly advantageous by providing a one-step process for removing aldehydes from crude acetone to produce acetone with improved purity.

In an embodiment, the method can include contacting an initial solution with a basic ion-exchange resin, wherein the initial solution includes acetone and acetone impurities. The initial solution can be crude acetone (i.e., acetone solution containing impurities) obtained from a reaction. Acetone impurities can be any reaction by-product in an acetone stream, including but not limited to, A-methyl styrene, acetophenone, hydroxyacetone, mesityl oxide, diacetone alcohol, acetaldehyde, propionaldehyde, methanol, and/or water. The acetone impurities can be removed from the initial solution with the basic ion-exchange resin to produce a purified solution. For example, for an initial solution containing acetaldehyde and propionaldehyde, a final acetaldehyde amount of acetaldehyde in the purified solution is less than an initial acetaldehyde amount of acetaldehyde in the initial solution, and a final propionaldehyde amount of propionaldehyde in the purified solution is less than an initial propionaldehyde amount of propionaldehyde in the initial solution.

The pH of the initial solution can be adjusted prior to contacting the ion-exchange resin by any suitable method. For example, the method can include adjusting the pH of the initial solution using about 20 to about 40 parts per million (ppm) of hydrogen chloride, for example 25 to 30 ppm. The pH of the initial solution can be 5 to 8, for example 6 to 7.

Exemplary ion-exchange resins for use in the methods disclosed herein can include basic anionic resins. The basic ion-exchange resin can be a basic polymer including ammonium functional groups, amine functional groups, sulphonium functional groups, or chloride, among others. For example, the basic ion-exchange resin can include a quaternary ammonium base, a tertiary amine base, a secondary amine base, a quaternary sulphonium base, or a combination comprising at least one of the foregoing. The resins may have a polystyrene backbone cross-linked with divinyl benzene. A quaternary ammonium salt such as trimethyl benzyl ammonium, dimethyl benzyl ethanol ammonium, etc., can be bonded to the polymer by a carbon-carbon bond. Commercially available ion-exchange resins can include, but are not limited to, DOW™ AMBERLYST™ A21, AMBERLITE™ IRC748, AMBERLITE™ IRA67, AMBERLITE™ IRA402, AMBERLITE™ IRA400, LEWATIT™ A 365, LEWATIT™ A 8071, LEWATIT™ A 8072, LEWATIT™ A 8073, LEWATIT™ A 8075 KR, LEWATIT™ MonoPlus MP 500, or a combination comprising at least one of the foregoing.

The ion-exchange resin can be treated with a bisulfite solution. For example, the resin can be immersed in an aqueous bisulfite solution of 5% to 15% bisulfite, for example 10% bisulfite. The resin can be allowed to stand in the bisulfite solution for greater than 8 hours, or greater than 10 hours, or greater than 12 hours, for example, 8 to 12 hours. In an embodiment, the resin is allowed to stand in the bisulfite solution for 12 hours. The bisulfite solution is removed, and the resin is washed with deionized water and dried under vacuum, typically below 10 millibars (mbar), in a rotovac evaporator until the moisture is removed.

The resin may be packed in a column to allow the initial solution to move through the column to remove the aldehydes resulting in a purified acetone solution. The ion-exchange resin loading in the column can be greater than 40% with respect to the quantity of acetone in the initial solution. In an example, the ion-exchange loading can be greater than or equal to 50%, for example, greater than or equal to 55%, for example, greater than or equal to 60% with respect to the quantity of acetone in the initial solution. The mass ratio of the acetone in the initial solution to ion-exchange resin can be greater than 0.1, greater than or equal to 0.4, for example, greater than or equal to 0.5, for example, greater than or equal to 0.6. The mass ratio of the acetone in the initial solution to ion-exchange resin can be less than 0.9, for example, less than 0.8, for example, less than 0.7. For example, the mass ratio of the acetone in the initial solution to ion-exchange resin can be 0.1 to 0.9, for example, 0.2 to 0.8, for example, 0.4 to 0.9, for example, 0.5 to 0.9.

The "KT-test" (permanganate test for time, an oxidation test using a solution of potassium permanganate) is widely used as an analytical test for determining the total quantity of aldehydes and other reducible impurities contained in commercial acetone. A large percentage of the acetone currently sold commercially on the market has a minimal KT-test value equal to about 2 hours. Using the systems and methods disclosed herein, it is possible to produce commercial (purified) acetone which has a KT-test time greater than 8 hours from initial acetone solutions having a KT-test time of less than 2 hours due to aldehyde impurities. In an example, the purified acetone produced from the present method can have a KT-test time greater than 8 hours, greater than 8.5 hours, or greater than 9 hours, as measured by the SABIC KT-Test method.

In an example, the method produces purified solution that has an acetaldehyde level of less than 10 ppm, for example, less than 5 ppm, for example, less than 1 ppm, for example, less than 0.5 ppm. The method can produce purified acetone that has a propionaldehyde level of less than 10 ppm, for example, less than 5 ppm, for example, less than 1 ppm, for example, less than 0.5 ppm.

FIG. 1 illustrates a schematic of an embodiment of a system 10 as described herein including a reactor 11 containing the initial solution including acetone and acetone impurities. The system 10 also includes a column 22 including an ion-exchange resin 28. The initial solution from the reactor 11 can pass through an in-line valve 18 and through a line 20 into a pump 14. Pump 14 can move the solution through line 24 and through column 22, wherein the initial solution can contact the ion-exchange resin 28. The purified solution can exit the column 22 through a column outlet 36, wherein the purified solution can pass through a line 26 and be collected in a container 12.

The line 16 can contain a heating fluid, such as oil, that circulates through the system 10. Specifically, the reactor 11 can be surrounded by a jacket 40, such as a hold oil jacket, wherein the heating fluid can enter the jacket 40 through a reactor inlet 42 and exit through a reactor outlet 38. Similarly, column 22 can be surrounded by a jacket 30 wherein the fluid from line 16 enters the jacket through a column inlet 32 and exits through a column outlet 34. The heating fluid can be heated to below the boiling point of the solvent, such as acetone.

EXAMPLES

Batches of 20 Liters of crude acetone test solution were prepared using reagent-grade chemicals, specifically high performance liquid chromatograph (HPLC) grade acetone having a purity of 99.9%, acetaldehyde, and propionaldehyde. The resulting prepared crude acetone solution contained 51.3 milligrams per liter (mg/L) of acetaldehyde and 55 mg/L propionaldehyde, as well as other impurities common to the process such as methanol and water. The pH of the prepared crude acetone solution was adjusted using dilute hydrochloride (HCl) resulting in a solution containing 25 ppm of HCl. The prepared crude acetone solution was then fed into the column and passed through the ion-exchange resin bed containing a treated ion-exchange resin. The flow rate can be 10 to 100 weight hourly space velocity (WHSV). The purified acetone solution was collected and the residual acid concentrations of impurities were determined using gas chromatography.

The treated ion-exchange resin was prepared by treating AMBERLITE IRA 400, commercially available from Sigma Aldrich, with 10 wt % sodium bisulfite in water for 12 hours to produce a bisulfite treated ion-exchange resin. The resin was washed with water and dried under vacuum, below 10 mbar, in a rotovac evaporator at 85-90° C. to remove the moisture.

Permanganate Test Procedure (KT-Test) (Also Referred to as the "SABIC KT-Test") was used to determine the KT-test values and the amount of acetaldehyde in the acetone. A graduated glass cylinder (50 ml) was filled with a sample of commercial acetone to the 50 ml mark. A 2 ml sample of a 0.02 wt % aqueous solution of potassium permanganate was added to the acetone sample and the solutions mixed well. The cylinder containing the acetone/potassium mixture was placed in a water bath maintained at 25° C. The color of the acetone/potassium permanganate mixture was observed every 30 minutes for loss of the red-purple color. The KT-Test value was determined by the number of hours required for the acetone/permanganate solution to fade to the orange-pink color of a standard color solution (prepared by dissolving 0.280 grams of uranyl nitrate hexahydrate and 0.170 grams of cobaltous chloride hexahydrate in 50 ml of distilled water).

A GC HP5890 gas chromatograph equipped with a dual flame ionization detector (FID) detector and using a 1 meter (m) by 5 millimeter (mm) (outside diameter) glass column packed with Cromosorb 102 on 80/100 Supelcoport measured acetaldehyde and propionaldehyde content in the purified samples. The gas chromatograph operating conditions included an oven temperature of 120° C., an injector temperature of 200° C., a detector temperature of 250° C., with an argon flow of 300 milliliters per minute (ml/min), a hydrogen flow of 30 ml/min, and an air flow of 300 ml/min. Total sample run time was 10 minutes. The acetaldehyde and propionaldehyde content levels were determined from a calibration cure obtained by injecting standard solutions of various concentrations of each aldehyde.

Example 1

Example 1 was performed with a 50% ion-exchange resin loading with respect to acetone quantity for the removal of acetaldehyde and propionaldehyde from the prepared acetone initial solution. Table 1 illustrates results of the purified acetone solution. Gas Chromatography analysis determined 100% reduction in aldehyde content in the purified acetone solution after the ion-exchange resin treatment. The product sample demonstrated a KT-test time greater than 8.5 hours. "ND" indicates not detected.

TABLE 1

| Before treatment | | After treatment | |
|---|---|---|---|
| Impurity Type | Concentration (PPM) | Impurity Type | Concentration (PPM) |
| Acetaldehyde | 51.3 | Acetaldehyde | ND |
| Propionaldehyde | 55 | Propionaldehyde | ND |

Example 2

Example 2 was performed with 10% ion-exchange resin loading with respect to acetone quantity for the removal of acetaldehyde and propionaldehyde from the prepared initial acetone solution. Table 2 illustrates results of the purified acetone. Gas Chromatography analysis determined incomplete removal of the aldehyde impurities in acetone product after the ion-exchange resin treatment. The product sample demonstrated a KT-test time less than 2 hours.

TABLE 2

| Before IER treatment | | After IER treatment | |
|---|---|---|---|
| Impurity Type | Concentration (PPM) | Impurity Type | Concentration (PPM) |
| Acetaldehyde | 51.3 | Acetaldehyde | 12 |
| Propionaldehyde | 55 | Propionaldehyde | 22 |

As shown in the examples, when a 50% ion-exchange resin loading with respect to acetone quantity is used the acetaldehyde and propionaldehyde are reduced to a point of no detection, essentially 100% reduction of aldehydes from the initial solution. As shown in Example 2, when a 10% ion-exchange resin loading with respect to the acetone quantity is used the acetaldehyde and propionaldehyde concentrations are reduced by greater than 50%.

The present method is an efficient and economical method for producing high-quality (i.e., purified) commercial acetone with the use of a single column.

The systems and methods of purifying acetone disclosed herein include at least the following embodiments:

Embodiment 1

A method for purifying acetone, comprising: contacting an initial solution with a basic ion-exchange resin at a temperature of 15° C. to 30° C., wherein the initial solution comprises acetone and acetone impurities; and removing the acetone impurities from the initial solution with the basic ion-exchange resin to produce a purified solution.

Embodiment 2

The method of Embodiment 1, wherein the basic ion-exchange resin is a basic ion-exchange resin treated with sodium bisulfite.

Embodiment 3

The method of Embodiment 1 or Embodiment 2, wherein the basic ion-exchange resin is a basic polymer including ammonium functional groups, amine functional groups, sulphonium functional groups, and chloride.

Embodiment 4

The method of any of Embodiments 1-3, further comprising treating the basic ion-exchange resin with sodium bisulfite prior to contacting the initial solution with the basic ion-exchange resin.

Embodiment 5

The method of Embodiment 4, wherein treating the basic ion-exchange resin includes contacting the basic ion-exchange resin with a treating solution of about 5 to about 15 wt % sodium bisulfite in water for greater than or equal to 10 hours.

Embodiment 6

The method of any of Embodiments 1-5, further including adjusting the pH of the initial solution using about 20 to about 40 parts per million of hydrogen chloride, prior to contacting the initial solution with the basic ion-exchange resin.

Embodiment 7

The method of any of Embodiments 1-6, wherein the mass ratio of acetone in the initial solution to ion-exchange resin is about 0.1 to about 0.9.

Embodiment 8

The method of any of Embodiments 1-7, further comprising collecting the purified solution after contacting the solution with the basic ion-exchange resin, wherein the purified solution includes acetone, wherein a final acetaldehyde amount of acetaldehyde in the purified solution is less than an initial acetaldehyde amount of acetaldehyde in the initial solution, and wherein a final propionaldehyde amount of propionaldehyde in the purified solution is less than an initial propionaldehyde amount of propionaldehyde in the initial solution.

Embodiment 9

The method of any of Embodiments 1-8, wherein the purified solution has an acetaldehyde level of less than about 10 parts per million as measured by gas chromatography from a calibration curve obtained using acetaldehyde/acetone standards.

Embodiment 10

The method of any of Embodiments 1-9, wherein the purified solution has a KT-Test time of greater than about 8.5 hours, as measured by the SABIC KT-Test method.

Embodiment 11

An acetone purification system, comprising: a reactor comprising an initial solution comprising acetone and acetone impurities; a column comprising an ion-exchange resin, wherein the column is connected to the reactor by a first line, wherein the first line includes a pump that directs the initial solution through the column to contact the basic ion-exchange resin; and a container for collecting a purified solution from the column, wherein the container is connected to the column by a second line.

Embodiment 12

The system of Embodiment 11, wherein the basic ion-exchange resin is a basic polymer including ammonium functional groups and chloride.

Embodiment 13

The system of Embodiment 11 or Embodiment 12, wherein the basic ion-exchange resin is a sodium bisulfite treated basic ion-exchanged resin.

Embodiment 14

The system of any of Embodiments 11-13, wherein the initial solution includes about 20 to about 40 parts per million of hydrogen chloride.

Embodiment 15

The system of any of Embodiments 11-14, wherein the mass ratio of acetone in the initial solution to ion-exchange resin is about 0.1 to about 0.9.

Embodiment 16

The system of any of Embodiments 11-15, wherein the initial solution includes acetone, acetaldehyde, and propionaldehyde, wherein the purified solution includes acetone, wherein a final acetaldehyde amount of acetaldehyde in the purified solution is less than an initial acetaldehyde amount of acetaldehyde in the initial solution, wherein a final propionaldehyde amount of propionaldehyde in the purified solution is less than an initial propionaldehyde amount of propionaldehyde in the initial solution.

Embodiment 17

The system of any of Embodiments 11-16, wherein the purified solution has an acetaldehyde level of less than about 10 parts per million as measured by gas chromatography from a calibration curve obtained using acetaldehyde/acetone standards.

Embodiment 18

The system of any of Embodiments 11-17, wherein the purified solution has a KT-Test time of greater than about 8.5 hours, as measured by the SABIC KT-Test method.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for purifying acetone, comprising:
    contacting an initial solution with a basic ion-exchange resin at a temperature of 15° C. to 30° C., wherein the initial solution comprises acetone and acetone impurities;
    removing the acetone impurities from the initial solution with the basic ion-exchange resin to produce a purified solution;
    contacting the basic ion-exchange resin with a treating solution of 5 to 15 wt % sodium bisulfite in water for greater than or equal to 10 hours prior to contacting the initial solution with the basic ion-exchange resin; and
    adjusting the pH of the initial solution to 5 to 8, prior to contacting the initial solution with the basic ion-exchange resin,
    wherein the basic ion-exchange resin is packed in a column to allow the initial solution to move through the column and an ion-exchange resin loading in the column is greater than 40% with respect to the quantity of acetone in the initial solution, and
    wherein the purified solution has an acetaldehyde level of less than 10 parts per million as measured by gas chromatography from a calibration curve obtained using acetaldehyde/acetone standards.

2. The method of claim 1, wherein the basic ion-exchange resin is a basic polymer including ammonium functional groups, amine functional groups, sulphonium functional groups, and chloride.

3. A method for purifying acetone, comprising:
    contacting an initial solution with a basic ion-exchange resin at a temperature of 15° C. to 30° C., wherein the initial solution comprises acetone and acetone impurities;
    removing the acetone impurities from the initial solution with the basic ion-exchange resin to produce a purified solution; and adjusting the pH of the initial solution using about 20 to about 40 parts per million of hydrogen chloride, prior to contacting the initial solution with the basic ion-exchange resin.

4. The method of claim 1, wherein the mass ratio of acetone in the initial solution to ion-exchange resin is about 0.1 to about 0.9.

5. The method of claim 1, further comprising collecting the purified solution after contacting the solution with the basic ion-exchange resin, wherein the purified solution includes acetone, wherein a final acetaldehyde amount of acetaldehyde in the purified solution is less than an initial acetaldehyde amount of acetaldehyde in the initial solution, and wherein a final propionaldehyde amount of propionaldehyde in the purified solution is less than an initial propionaldehyde amount of propionaldehyde in the initial solution.

6. The method of claim 1, wherein the purified solution has a KT-Test time of greater than about 8.5 hours, as measured by the SABIC KT-Test method.

7. An acetone purification system, comprising:
a reactor comprising an initial solution comprising acetone and acetone impurities;
a column comprising an ion-exchange resin, wherein the column is connected to the reactor by a first line, wherein the first line includes a pump that directs the initial solution through the column to contact the basic ion-exchange resin; and
a container for collecting a purified solution from the column, wherein the container is connected to the column by a second line;
wherein at least one of
(i) the initial solution includes about 20 to about 40 parts per million of hydrogen chloride; or
(ii) the system further comprises
a jacket surrounding the column;
a column inlet through which a heating fluid enters the jacket; and
a column outlet through which the heating fluid exits the jacket,
the basic ion-exchange resin is packed in the column to allow the initial solution to move through the column and an ion-exchange resin loading in the column is greater than 40% with respect to the quantity of acetone in the initial solution,
the basic ion-exchange resin is a sodium bisulfite treated basic ion-exchanged resin,
the pH of the initial solution is 5 to 8, and
the purified solution has an acetaldehyde level of less than 10 parts per million as measured by gas chromatography from a calibration curve obtained using acetaldehyde/acetone standards.

8. The system of claim 7, wherein the basic ion-exchange resin is a basic polymer including ammonium functional groups and chloride.

9. The system of claim 7, wherein the initial solution includes about 20 to about 40 parts per million of hydrogen chloride.

10. The system of claim 7, wherein the mass ratio of acetone in the initial solution to ion-exchange resin is about 0.1 to about 0.9.

11. The system of claim 7, wherein the initial solution includes acetone, acetaldehyde, and propionaldehyde, wherein the purified solution includes acetone, wherein a final acetaldehyde amount of acetaldehyde in the purified solution is less than an initial acetaldehyde amount of acetaldehyde in the initial solution, wherein a final propionaldehyde amount of propionaldehyde in the purified solution is less than an initial propionaldehyde amount of propionaldehyde in the initial solution.

12. The system of claim 7, wherein the purified solution has a KT-Test time of greater than about 8.5 hours, as measured by the SABIC KT-Test method.

13. The system of claim 7, wherein
the system further comprises
a jacket surrounding the column;
a column inlet through which a heating fluid enters the jacket; and
a column outlet through which the heating fluid exits the jacket,
the basic ion-exchange resin is packed in the column to allow the initial solution to move through the column and an ion-exchange resin loading in the column is greater than 40% with respect to the quantity of acetone in the initial solution,
the basic ion-exchange resin is a sodium bisulfite treated basic ion-exchanged resin,
the pH of the initial solution is 5 to 8, and
the purified solution has an acetaldehyde level of less than 10 parts per million as measured by gas chromatography from a calibration curve obtained using acetaldehyde/acetone standards.

14. The system of claim 7, wherein the initial solution has a KT-test time of less than 2 hours.

15. The method of claim 1, wherein the initial solution has a KT-test time of less than 2 hours.

\* \* \* \* \*